US007825287B2

(12) United States Patent
Ahn et al.

(10) Patent No.: US 7,825,287 B2
(45) Date of Patent: Nov. 2, 2010

(54) PROCESS FOR PRODUCTION OF TRIPTANE AND TRIPTENE

(75) Inventors: John Ahn, Berkeley, CA (US); Burcin Temel, El Cerrito, CA (US); Enrique Iglesia, Moraga, CA (US)

(73) Assignee: The Regents of the University of California, Oakland, CA (US)

( * ) Notice: Subject to any disclaimer, the term of this patent is extended or adjusted under 35 U.S.C. 154(b) by 383 days.

(21) Appl. No.: 12/058,300

(22) Filed: Mar. 28, 2008

(65) Prior Publication Data

US 2009/0247803 A1 Oct. 1, 2009

(51) Int. Cl.
*C07C 1/00* (2006.01)

(52) U.S. Cl. ...................................... 585/640; 585/733

(58) Field of Classification Search ................ 585/640, 585/733

See application file for complete search history.

(56) References Cited

U.S. PATENT DOCUMENTS

| | | | | |
|---|---|---|---|---|
| 3,082,272 | A * | 3/1963 | Long .......................... | 585/254 |
| 4,059,646 | A | 11/1977 | Wald et al. | |
| 4,059,647 | A | 11/1977 | Wald et al. | |
| 4,126,642 | A | 11/1978 | Kim et al. | |
| 4,151,214 | A | 4/1979 | Kim et al. | |
| 4,166,189 | A | 8/1979 | Wald et al. | |
| 4,209,031 | A | 6/1980 | Sutton | |
| 4,373,109 | A | 2/1983 | Olah | |
| 4,508,618 | A | 4/1985 | Olah | |
| 6,855,857 | B2 | 2/2005 | Boesveld et al. | |
| 7,067,448 | B1 | 6/2006 | Weitakamp et al. | |
| 2004/0133055 | A1 | 7/2004 | Cook et al. | |
| 2004/0249228 | A1 | 12/2004 | Boesveld et al. | |
| 2005/0182278 | A1 | 8/2005 | Canos et al. | |
| 2007/0032692 | A1 | 2/2007 | O'Rear et al. | |

FOREIGN PATENT DOCUMENTS

WO WO 2009/063177 * 5/2009

OTHER PUBLICATIONS

Biscardi, Joseph A. et al.; "Structure and function of metal cations in light alkane reactions catalyzed by modified H-ZSM5"; 1996, *Catalysis Today*, vol. 31, pp. 207-231.

Chang, Clarence D. et al.; "The Conversion of Methanol and Other O-Compounds to Hydrocarbons over Zeolite Catalysts"; 1977, *Journal of Catalysis*, vol. 47, pp. 249-259.

Cormerais, F.X. et al.; "Selectivity of the-dimethylether to hydrocarbons conversion on various zeolites"; 1981, *Zeolites*, vol. 1, pp. 141-144.

Cormerais, F.X. et al.; "Acid Strength of the Catalytic Sites Responsible for the Conversion of Dimethyl Ether into Hydrocarbons in Y Zeolites"; 1981, *J. Chem. Research,* pp. 290-291.

Hutchings, Graham J. et al.; "Methanol conversion to hydrocarbons over zeolite H-ZSM-5: Comments on the formation of $C_4$ hydrocarbons at low reaction temperatures"; 1993, *Applied Catalysis A*, vol. 106, pp. 115-123.

Hutchings, Graham J. et al.; "The Conversion of Methanol and Other O-Compounds to Hydrocarbons over Zeolite β"; 1994, *Journal of Catalysts*, vol. 147, pp. 177-185.

Iglesia, Enrique et al.; "Isomerization of Alkanes on Sulfated Zirconia: Promotion by Pt and by Adamantyl Hydride Transfer Species"; 1993, *Journal of Catalysts*, vol. 144, pp. 238.253.

Keil, Frerich J.; "Methanol-to-hydrocarbons: process technology"; 1999, *Microporous and Mesoporous Materials*, vol. 29, pp. 49-66.

Kolboe, Stein; "Methanol Reactions on ZSM-5 and Other Zeolite Catalysts: Autocatalysis and Reaction Mechanism"; 1986, *Akta Chemica Scandinavica*, vol. A40, pp. 711-713.

Lunsford, Jack H.; Catalytic conversion of methane to more useful chemicals and fuels: a challenge for the 21st century; 2000, *Catalysis Today*, vol. 63, pp. 165-174.

Mikkelsen, O. et al.; "The conversion of methanol to hydrocarbons over zeolite H-beta"; 1999, *Microporous and Mesoporous Materials*, vol. 29, pp. 173-184.

Ravichandran, G. et al.; "Selective synthesis of $C_2$-$C_4$ hydrocarbons from CO +$H_2$ on composite catalysts"; 1993, *Catalysis Letters*, vol. 22, pp. 179-187.

Salvador, Pedro et al.; "Surface Reactivity of Zeolites Type H-Y and Na-Y with Methanol"; 1976, *Reactivity of Zeolites*, pp. 1153-1168.

Schulz, Hans et al.; Deactivation and thermal regeneration of zeolite HZSM-5 for methanol conversion at low temperature (260-290C), 1999, *Microporous and Mesoporous Materials*, vol. 29, pp. 205-218.

Sodesawa, T.; "Methanol Conversion to Lower Hydrocarbons over Proton Exchanges NaY Zeolite Catalysts"; 1986, *React. Kinet. Catal. Lett.*, vol. 32, No. 2, pp. 251-255.

Stocker, Michael; "Methanol-to-hydrocarbons: catalytic materials and their behavior"; 1999, *Microporous and Mesoporous Materials*, vol. 29, pp. 3-48.

Valyon, J. et al.; "The Influence of Adamantane on the Reaction of *n*-Heptane over H-Y, H-β and H-Mordenite Zeolites"; 1998, *React. Kinet. Catal. Lett.*, vol. 64, No. 1, pp. 177-184.

Valyon, J. et al.; "The activation of $CD_4$ for H/D exchange over H-zeolites"; 2002, *Catalysis Letters*, vol. 82, No. 1-2, pp. 29-35.

Valyon, J. et al.; "The effect of adamantine addition on the conversion of *n*-heptane over H- and Pt/H-zeolites"; 2002, *Applied Catalysis A*, vol. 229, pp. 135-146.

(Continued)

*Primary Examiner*—In Suk Bullock
(74) *Attorney, Agent, or Firm*—Townsend and Townsend and Crew LLP

(57) ABSTRACT

High octane $C_7$ hydrocarbons, particularly 2,2,3-trimethylbutane ("triptane") and 2,2,3-trimethyl-but-1-ene ("triptene") (collectively "triptyls") are produced by homologation of a feed comprising dimethyl ether and/or methanol and optionally including one or more aliphatic hydrocarbons in the presence of certain acidic zeolite catalysts. The process can be carried out at temperatures lower than those previously used for conversion of dimethyl ether and/or methanol to higher alkanes, including $C_7$ alkanes, and results in selective production of triptane and/or triptene with relatively little isomerization to or production of other $C_7$ alkanes.

21 Claims, No Drawings

OTHER PUBLICATIONS

Venuto, P.B. et al.; “Organic Catalysis over Crystalline Aluminosilicates”; 1968, *Advances in Catalysis and Related Subjects*, vol. 18, pp. 259-371.

Bu, Xianhui et al.; “Large-Cage Zeolite Structures with Multidimensional 12-Ring Channels”; 1997, *Science*, vol. 278, pp. 2080-2085.

Corma, Avelino et al.; “ITQ-15: The first ultralarge pore zeolite with a bi-directional pore system formed by intersecting 14- and 12-ring channels, and its catalytic implications”; 2004, *Chem. Commun.*, pp. 1356-1357.

Sugi, Yoshihiro et al.; “The Alkylation of Biphenyl over Fourteen-Membered Ring Zeolites. The Influence of Zeolite Structure and Alkylating Agent on the Selective for 4,4’-Dialkyliphenyl”; 2007, *Bulletin of the Chemical Abstracts* of Japan, vol. 80, pp. 1418.

* cited by examiner

PROCESS FOR PRODUCTION OF TRIPTANE AND TRIPTENE

BACKGROUND OF THE INVENTION

This invention relates to a process for production of higher alkanes, and particularly for production of the $C_7$ hydrocarbons 2,2,3-trimethylbutane (also known as "triptane") and 2,2,3-trimethylbut-1-ene (also known as "triptene") by homologation of dimethyl either and/or methanol, in a feed containing the same. Collectively, these two compounds will be referred to herein as "triptyls". In general, processes that produce triptane may also produce triptene, which may be wholly or partly converted to triptane during the process. Both compounds have equivalently high octane numbers.

It has been known for quite some time that certain branched hydrocarbons, and triptyls in particular, provide high octane properties to fuels such as gasoline and jet fuel. U.S. Pat. No. 6,855,857 of Boesveld et al. describes a process for selectively isomerizing hydrocarbons including paraffinic hydrocarbons (both cyclic and acyclic), alkyl-substituted aromatic hydrocarbons, or mixtures of such hydrocarbons, in the presence of a Lewis acid isomerization catalyst, notably a transition metal halide or salt of fluorosulfuric, trifluoromethanesulfonic, or trifluoroacetic acid. Selectivity to triptane of from about 8 to about 16% is reported.

US published patent application 2004/249228 of Boesveld et al. describes a process for producing triptane from a mixed fed containing both cyclic and acyclic hydrocarbons, with preferably at least 30% of the feed being acyclic hydrocarbons, and preferably primarily $C_7$ hydrocarbons, using a combination catalyst having both a metal function and an acidic function. The acidic function is preferably provided by a zeolite, preferably a faujasite-type zeolite such as ECR-30, ECR-32, ZSM-5, ZSM-3 or ZSM-20. U.S. Pat. No. 4,508,618 of Olah et al. describes a process for increasing the octane number of natural gasoline using a trifluoromethanesulfonic acid catalyst. However, very little triptane was produced in the sole example in that patent.

Technologies for producing gasoline fractions, including triptane, from dimethyl ether and/or methanol, have been investigated for a good number of years. For example, U.S. Pat. Nos. 4,059,646 (Wald et al.), 4,059,647 (Wald et al.), 4,126,642 (Kim et al.), 4,151,214 (Wald et al.) 4,166,189 (Wald et al.), and 4,209,031 (Drent et al.), and US published application 2004/133055 (Cook et al.) describe processes for production of triptane from dimethyl ether and/or methanol using various zinc halide catalysts. US published application 2007/004955 (Kay et al.) describes a process for producing triptane from dimethyl ether and/or methanol using an indium halide catalyst. However, halide catalysts and other halide-containing materials have the disadvantage of introducing metallurgical complexity in the overall process due to corrosion and the leaching of halides as part of the products stream.

Previous work by researchers at Mobil Oil Company describe production of gasoline and of light olefins from dimethyl ether and/or methanol ("MTG" or "methanol-to-gasoline" and "MTO" or "methanol-to-olefins" processes, respectively) using various acidic zeolites. Temperatures were approximately 573K, and there was little selectivity to triptane.

It would be desirable to possess a process for production, especially selective production, of triptane from dimethyl ether and/or methanol. Such a process is provided by this invention. It would be particularly useful to carry out such processes with reactants and most products in the gas phase and without the use of halides.

BRIEF SUMMARY OF THE INVENTION

In brief, the invention relates to a process for producing higher octane $C_7$ hydrocarbons, particularly triptane and/or triptene from a feed comprising dimethyl ether and/or methanol, by contacting said feed with an acidic zeolite catalyst having a structure that comprises at least one connecting channel that contains a twelve-or fourteen-membered ring at a temperature of from about 125° C. to about 275° C.

DETAILED DESCRIPTION OF THE INVENTION

In brief, the invention relates to a process for producing higher octane $C_7$ hydrocarbons, particularly triptane and/or triptene from a feed comprising dimethyl ether and/or methanol, by contacting said feed with an acidic zeolite catalyst having a structure that comprises at least one connecting channel that contains a twelve-or fourteen-membered ring at a temperature of from about 125° C. to about 275° C.

The feed to the process may comprise primarily or substantially only dimethyl ether, primarily or substantially only methanol, or a mixture of the two, particularly mixtures in which methanol or dimethyl ether is the major constituent and the other is present in a minor amount, for example as an impurity or a by-product from a previous step for production of the major constituent. The feed may also contain other components, depending on its source. For example, if the feed comprises methanol produced from synthesis gas, the feed may contain other products of such a process, such as formaldehyde, methyl formate, methyl acetate, carbon monoxide, carbon dioxide, hydrogen and water. Preferably, however, such other components (or at least the major portion of them) are removed from the feed or converted to methanol and/or dimethyl ether prior to the feed's being introduced into the process for production of triptyls so that their diluting effect is minimized. As described below, the feed may also contain one or more aliphatic hydrocarbons.

The catalysts suitable for the conduct of the processes of this invention are acidic zeolite catalysts whose structures comprise at least one connecting channel that contains a twelve-or fourteen-membered ring. They are in the class known as "large pore" zeolites. Examples of such zeolites having a twelve-membered ring are H-FAU (faujasite) (7.4×7.4 Å), H-BEA (beta) (5.6×5.6 and 6.6×6.7 Å), H—X, H—Y, H—CON, H-EMT, H—ISV, H-MEI, and H-SAO zeolites. Examples of acidic zeolites having a fourteen-membered ring are H-AEI, H—CFI, H-DON and H—OSO. Information about such zeolites is available on the website of the International Zeolite Association at www.iza-online.org Preferred zeolites of this invention are aluminosilicate zeolites; however, some of the Si atoms in the framework may be replaced by trivalent atoms such as Al, B, Ga, Fe or by bivalent atoms such as Be or Zn, or by a combination thereof, or ion-exchanged or loaded with one or more metals such as copper, nickel, iridium, rhodium, platinum, palladium, cobalt, boron, gallium, zinc and/or iron. Framework modifier elements to both types of catalysts may be introduced to the framework by any conventional means. Where a framework modifier element is used in a catalyst for this process, the catalyst suitably has a ratio of silica to the oxide of the framework modifier element of from about 10:1 to about 100:1.

The zeolites useful in this invention may have side-pockets and/or cages within the zeolite structure. For the purposes of the present invention, the term 'zeolite' also includes materials having a zeolite-type structure such as delaminated porous crystalline oxide materials such as MCM and pillared layered oxide materials such as ITQ. For the purpose of this invention the zeolites must be in the acid or H— form since acidic sites are known to be required for the necessary homologation reactions to proceed. However, the zeolites may also contain a relatively small content of metals such as alkalines so long as the content does not affect their essentially acidic nature.

Zeolites are available from commercial sources. Alternatively they may be synthesized using known techniques. In general, synthetic zeolites are prepared from aqueous reaction mixtures comprising sources of appropriate oxides. Organic directing agents may also be included in the reaction mixture for the purpose of influencing the production of a zeolite having the desired structure. After the components of the reaction mixture are properly mixed with one another, the reaction mixture is subjected to appropriate crystallization conditions. After crystallization of the reaction mixture is complete, the crystalline product may be recovered from the remainder of the reaction mixture. Such recovery may involve filtering the crystals, washing with water followed by a calcination treatment at high temperature. The synthesis of zeolites is described in numerous references.

The zeolite catalyst for use in the process of the present invention is used in the acid form, generally referred to as the 'H' form of the zeolite, for example, H-faujasite, H-beta, etc. Other forms of the zeolite, such as the $NH_4$ form can be converted to the H-form, for example, by calcining the $NH_4$ form at elevated temperature. The acid form of a zeolite will possess Brønsted acid ($H^+$) sites which are distributed among the various channel systems in the zeolite. The number or concentration of $H^+$ species residing in any particular channel system can be determined by known techniques such as infrared and NMR spectroscopic techniques.

The process is carried out at lower temperatures than prior art processes using these or other types of zeolites. For instance, Mikkelsen et al., *Microporous and Mesoporous Materials* 29:173 (1999) described a process for conversion of methanol to hydrocarbons using H-BEA zeolite at 400° C. The primary products were $C_2$-$C_4$ hydrocarbons and polymethyl benzenes. The chromatogram (FIG. 6) does not show any peak for C7 alkanes. Temperatures for the process of this invention generally range from about 125 to about 275° C., preferably from about 150 to about 250° C. and most preferably from about 180 to about 220° C., as opposed to temperatures used in the Mobil MTG work, which tended to be above about 300° C. As demonstrated in the examples below, operating at lower temperatures in this range has been shown to enhance selectivity to triptane.

In general, the process is run at pressures of from about 0.5 to about 15, preferably from about 2 to about 5 bar dimethyl ether or from about 0.1 to about 30, preferably from about 4 to about 10 bar methanol. Typical DME space velocities are from 0.16 mol $g^{-1}$ $h^{-1}$ to 1.7 mol $g^{-1}$ $h^{-1}$. As demonstrated in the examples below, operation at higher dimethyl ether pressures can result in an increased rate of formation of triptyls and/or higher triptyls turnovers (amount of product per unit of active catalyst area per unit of time) (based on aluminum content of the zeolite). Operation at a combination of both higher partial pressures of dimethyl ether and/or methanol and lower temperatures than the prior art tend to produce the best results in terms of selectivity to triptyls.

The processes of this invention may be run in equipment ranging in size from microreactors (e.g., microchannel reactors) to full-sized commercial process equipment. A commercial installation will include typical process expedients such as recycle streams and catalyst recycle expedients, for efficient use of reactants and reaction products, and may be integrated with process units for further processing and separation of the reaction products. Reaction products that may be recovered and either sold, recycled to the reactor or sent to other processing units include isobutane and hexamethylbenzene. Reactors may be fixed-bed, fluidized-bed, moving bed, ebullient bed, bubble column, and other types suitable for use with zeolite catalysts.

The process may be run as either a continuous or a batch process, with continuous processes typically preferred. In operating the process, unreacted starting materials may be recovered and recycled to the reactor. Side products may be recovered and either sent for further processing or recycled to the reactor, as appropriate. Isobutane, for instance, is typically produced as a side product in this process, and can be recycled to the reactor. Spent catalyst may be regenerated by known techniques, either in the reactor or externally, and reused.

The conduct of the process can be enhanced by the addition of a hydrogen donor or hydrogen transfer co-catalyst, to the feed, preferably in ratios defined below. These function so as to increase the rate of hydrogen transfer and decrease cracking rates relative to homologation by removing adsorbed species, especially triptyl cations, before they can grow larger and/or crack. The preferred hydrogen donor is adamantane. Tetralin, hexamethylcyclohexane, and decalin are suitable hydrogen transfer co-catalysts. Adamantane may be used in a molar ratio relative to dimethyl ether and/or methanol of from about 0.005:1 to about 0.05:1. Tetralin, hexamethylcyclohexane or decalin may be used in a molar ratio relative to dimethyl ether and/or methanol of from about 0.1:1 to about 0.3:1.

The process can also be enhanced by the inclusion in the feed of various aliphatic hydrocarbons, which can provide hydrogen atoms required to form alkanes from methanol or DME without the concurrent rejection of hydrogen from hydrocarbons to form undesired aromatic molecules (e.g. hexamethylbenzene), as well as additional hydrocarbon material to assist in or participate in homologation of lower alkanes or alkenes to produce triptyls. The hydrocarbons included in the feed are preferably lower alkanes and/or alkenes, such as isobutane, butane, isobutene, 2-methylpentane, 2,3-dimethylbutane, and corresponding olefins. Higher molecular weight hydrocarbons, including materials such as those produced in Fischer-Tropsch processes, may be added to the feed so long as they will either produce the necessary hydrogen to assist in the process or crack or otherwise convert to lower hydrocarbons that can assist homologation. The hydrocarbons may be added as fresh feed and/or may be materials recovered and recycled from the process reactor. Such hydrocarbons may be included in the feed in a molar ratio, with respect to dimethyl ether or methanol, of from about 0.1:1 to about 5:1, preferably from about 0.3:1 to about 3:1. Thus, in some instances the process may be viewed as one in which a minor amount of the above-described hydrocarbons is included in the feed that comprises dimethyl ether and/or methanol. On the other hand, if the ratio of hydrocarbons to dimethyl ether and/or methanol is greater than one, up to about 5:1, the process could be viewed as a process for the production of triptyls from a feed comprising one or more hydrocarbons, with a minor amount (20% or more) of dimethyl ether and/or methanol. Both types of such processes are within the concepts of this invention.

The process of this invention has been found to selectively produce triptane and also its olefinic analog triptene (2,3,3-trimethyl-1-butene). By "selectively" is meant that the C7 fraction of the product contains at least about 20%, and preferably at least about 25%, triptyls. As shown in the examples below, selectivity to triptane can be over 80% at lower temperatures, based on the amount of overall $C_7$ products formed. Percent conversion of the dimethyl ether and/or methanol to $C_7$ products can be as high as 100% and C7 products can be maximized by recycling of the unconverted alkanes as shown above. In addition, the process of the invention produces a product having a relatively low content of aromatics such as polymethylbenzenes. This is in contrast to a number of prior art processes that produce a product having appreciable quantities of such aromatics.

EXAMPLES

The following are representative examples of processes according to the invention. However, they are presented as illustrative only, and not as limitations on the nature of the invention.

Zeolites $NH_4$—FER (ferrierite) (Si/Al=10:1; Zeolyst), $NH_4$-MOR (mordenite) (Si/Al=10:1; Zeolyst), $NH_4$-ZSM5 (Si/Al=15:1; Zeolyst), $NH_4$—USY (Si/Al=3:1; Engelhard), and $NH_4$-BEA (beta) (Si/Al=12.5:1; Zeolyst) were treated in flowing dry air (~1.67 $cm^3\ s^{-1}$) at 773 K for 10 h to form acid zeolites.

The catalyst evaluation and butene addition experiments were carried out in a quartz plug-flow reactor (12.5 mm OD) containing zeolites (0.15 g-0.25 g, 180-250 μm) held on a porous quartz disc. The temperatures were regulated with a Watlow® controller (Series 989) and resistively heated furnace. Catalysts were treated in dry air (~0.83 $cm^3\ s^{-1}$) for 2 h at 773 K and cooled to reaction temperature (473 K, 200° C.) in flowing He (0.83 $cm^3\ s^{-1}$, UHP, Praxair) before introducing dimethyl ether (DME) (99.5%, Matheson), Ar (99.999%, Praxair), 1-butene (99%, Scott Specialty Gases) or isobutene (99% Matheson) The reactor effluents were transferred in heated lines and analyzed by on-line gas chromatograph (Agilent® 6890), equipped with a methyl silicone column (HP-1, 50 m×0.32 mm×1.05 μm) connected to a flame ionization detector and a Porapak® Q column (80-100 mesh, 12 ft×⅛ in.) connected to a thermal conductivity detector.

The pressure and temperature variation experiments were carried out using a stainless steel, plug-flow reactor (9.5 mm OD) containing zeolites (0.4-1.6 g, 180-250 μm) held in place by quartz wool. The temperatures were regulated with a Watlow controller (Series 988) and furnace equipped with three thermocouples aligned along the tube center. The catalysts were treated by the procedure described above before introducing DME at the reaction temperatures (453-493 K or 180-220° C.). Results are shown in Tables 1-5 below.

TABLE 1

Summary of catalyst screening results in a tubular plug-flow reactor, 60 kPa DME, 473 K (200° C.), after 4800 s, 0.25 g catalyst, 0.20 $cm^3s^{-1}$ total flow rate.

| Catalyst | H-FER | H-MFI | H-MOR | H-FAU | H-BEA |
|---|---|---|---|---|---|
| Channel size | 10 × 8 | 10 × 10 | 12 × 8 | 12 × 12 | 12 × 12 |
| Si/Al ratio | 10 | 15 | 10 | 3 | 12.5 |
| % Conversion to hydrocarbons | >0.1 | 2.2 | 0.3 | 7.9 | 2.6 |
| % $C_7$ in products | 0 | 5.2 | 2.6 | 7.6 | 21 |
| % Triptyls in $C_7$ | 0 | 11 | 59 | 46 | 72 |
| DME to hydrocarbons conversion rate ($10^{-3}$ mol Carbon [s mol Al]$^{-1}$) | $1.5 \times 10^{-2}$ | $6.1 \times 10^{-1}$ | $7.4 \times 10^{-2}$ | $8.6 \times 10^{-1}$ | $7.4 \times 10^{-1}$ |
| Triptyl formation rate ($10^{-3}$ mol [s mol Al]$^{-1}$) | 0 | $4.9 \times 10^{-4}$ | $1.6 \times 10^{-4}$ | $4.3 \times 10^{-3}$ | $1.6 \times 10^{-2}$ |

TABLE 2

Effects of DME pressure variation on selectivities at 473 K (200° C.), 0.4 g HBEA (Si/Al = 12.5), 0.28 $cm^3s^{-1}$ total flow rate, at the same DME to hydrocarbons conversion rate ($3.8 \times 10^{-4}$ mol Carbon [s mol Al]$^{-1}$).

| DME (kPa) | $C_4/C_7$ ratio | $C_7$ in hydrocarbons selectivity % | Triptyls in $C_7$ selectivity % |
|---|---|---|---|
| 60 | 1.1 | 28 | 75 |
| 125 | 0.93 | 30 | 80 |
| 250 | 0.87 | 32 | 83 |

TABLE 3

Effects of temperature variation on deactivation constant ($k_d$; exponential decay) and selectivities at 473 K (200° C.), 1.6 g HBEA (Si/Al = 12.5), 0.28 $cm^3s^{-1}$ total flow rate, at ~110 ks time on stream. The selectivities were nearly independent of the observed conversion range.

| Temperature (K) | $k_d$ ($ks^{-1}$) | % $C_7$ in hydrocarbons selectivity | % Triptyls in $C_7$ selectivity |
|---|---|---|---|
| 453 | 0.0027 | 33 | 88 |
| 473 | 0.0056 | 29 | 81 |
| 493 | 0.0093 | 26 | 75 |

TABLE 4

Effects of cis-butene, 2,3-dimethylbutane (2,3DMB), and 2,3DMB with adamantane addition on rates and triptyls in $C_7$ selectivity at 473 K (200° C.), 0.15 g HBEA (Si/Al = 12.5), 0.17 $cm^3s^{-1}$ total flow rate. Amount of increase in rate of triptyl is indicated in parenthesis.

| Reactants | DME (60 kPa) | DME (60 kPa) butene (3 kPa) | DME (60 kPa) 2,3DMB (40 kPa) | DME (60 kPa) 2,3DMB (40 kPa) Adamantane (~0.1 kPa) |
|---|---|---|---|---|
| Triptyl formation rate ($10^{-3}$ mol [s mol Al]$^{-1}$) | $1.4 \times 10^{-2}$ | $4.5 \times 10^{-2}$ (3.3) | $2.7 \times 10^{-2}$ (1.93) | $3.3 \times 10^{-2}$ (2.36) |
| Triptyl selectivity in $C_7$ | 78 | 72 | 77 | 78 |

TABLE 5

Effects of 2,3-dimethylbutane and adamantane addition on rates and olefin to paraffin ratios (rate of hydrogen transfer indicator), triptyl in $C_7$ selectivity, and i-$C_4$s/triptyls ratio at 473 K (200° C.), 0.15 g HBEA (Si/Al = 12.5), 0.17 $cm^3s^{-1}$ total flow rate. Increase is indicated in parenthesis for rate of triptane.

| Reactants | DME (60 kPa) | DME (60 kPa) 2,3DMB (40 kPa) | DME (60 kPa) Adamantane (~0.1 kPa) | DME (60 kPa) 2,3DMB (40 kPa) Adamantane (~0.1 kPa) |
|---|---|---|---|---|
| Triptyl formation rate ($10^{-3}$ mol [s mol Al]$^{-1}$) | $1.4 \times 10^{-2}$ | $2.7 \times 10^{-2}$ (1.93) | $1.3 \times 10^{-3}$ | $3.3 \times 10^{-2}$ (2.36) |
| $C_5$ olefin/paraffin ratio | 1.32 | 1.28 | 0.99 | 0.97 |
| Triptyl selectivity in $C_7$ | 78 | 77 | 77 | 78 |
| i-$C_4$s/triptyls ratio | 1.32 | 1.24 | 1.36 | 1.01 |

The foregoing descriptions are offered primarily for purposes of illustration. Further modifications, variations and substitutions that still fall within the spirit and scope of the invention will be readily apparent to those skilled in the art. All such modifications coming within the scope of the appended claims are intended to be included therein.

All publications, patents, and patent applications cited herein are hereby incorporated by reference in their entirety for all purposes.

What is claimed is:

1. A process for producing triptane and/or triptene from a feed comprising dimethyl ether and/or methanol, comprising contacting said feed with an acidic zeolite catalyst having a structure that comprises at least one connecting channel that contains a twelve-or fourteen-membered ring at a temperature of from about 125° C. to about 275° C.

2. A process according to claim 1 in which the feed comprises dimethyl ether.

3. A process according to claim 1 in which the feed comprises methanol.

4. A process according to claim 1 in which the feed comprises a mixture of dimethyl ether and methanol.

5. A process according to claim 1 in which the temperature is from about 150 to about 250° C.

6. A process according to claim 1 in which the temperature is from about 180 to about 220° C.

7. A process according to claim 1 in which the feed further comprises a hydrogen donor or hydrogen transfer co-catalyst.

8. A process according to claim 7 in which the feed further comprises adamantane.

9. A process according to claim 8 in which the feed comprises adamantane in a molar ratio with respect to dimethyl ether and/or methanol of from about 0.005:1 to about 0.05:1.

10. A process according to claim 7 in which the feed further comprises tetralin, hexamethylcyclohexane or decalin.

11. A process according to claim 10 in which the molar ratio of tetralin, hexamethylcyclohexane or decalin with respect to dimethyl ether and/or methanol is from about 0.1:1 to about 0.3:1.

12. A process according to claim 1 in which the feed further comprises one or more aliphatic hydrocarbons.

13. A process according to claim 12 in which the feed comprises one or more aliphatic hydrocarbons that can serve as hydrogen donors, can contribute to a homologation process, or can be transformed under conditions of the process to one or more hydrocarbons that can serve as hydrogen donors or contribute to a homologation process.

14. A process according to claim 12 in which the molar ratio of said one or more aliphatic hydrocarbons to dimethyl ether and/or methanol in the feed is from about 0.1:1 to about 5:1.

15. A process according to claim 12 in which the molar ratio of said one or more aliphatic hydrocarbons to dimethyl ether and/or methanol in the feed is from about 0.3:1 to about 3:1.

16. A process according to claim 1 in which the acidic zeolite catalyst has a structure that comprises at least one connecting channel that contains a 12-membered ring.

17. A process according to claim 1 in which the acidic zeolite catalyst comprises H-FAU zeolite.

18. A process according to claim 1 in which the acidic zeolite catalyst comprises H-BEA zeolite.

19. A process according to claim 1 in which the acidic zeolite catalyst has a structure that comprises at least one connecting channel that contains a 14-membered ring.

20. A process according to claim 1 in which the zeolite catalyst further comprises one or more metals selected from the group consisting of aluminum, boron, gallium, iron, beryllium, zinc, copper, nickel, iridium, rhodium, platinum, palladium, cobalt, and indium.

21. A process according to claim 1 further comprising recovering one or more aliphatic hydrocarbons from the products of the reaction and recycling them to the feed.

* * * * *